United States Patent [19]
Jiang

[11] Patent Number: 5,907,389
[45] Date of Patent: May 25, 1999

[54] REMOTE-CONTROLLED LCD SIGHT-TESTING INSTRUMENT

[76] Inventor: J. J. Jiang, 1f, No. 7-2, Chung Yang Second St., Hsintien City, Taipei Hsien, Taiwan

[21] Appl. No.: 09/028,490

[22] Filed: Feb. 24, 1998

[51] Int. Cl.⁶ ........................................ A61B 3/00
[52] U.S. Cl. ............................................. 351/243
[58] Field of Search ................................. 351/205, 211, 351/221, 210, 212, 247, 222, 243, 244

[56] References Cited

U.S. PATENT DOCUMENTS

| | | | |
|---|---|---|---|
| 4,550,990 | 11/1985 | Trispel et al. | 351/243 |
| 5,790,234 | 8/1998 | Matsuyama | 351/212 |
| 5,793,469 | 8/1998 | Feiertag | 351/221 |

*Primary Examiner*—George Manuel
*Attorney, Agent, or Firm*—Rosenberg, Klein & Bilker

[57] ABSTRACT

A remote-controlled LCD sight-testing instrument which includes a mainframe and a remote controller, the mainframe having a display module, the display module being controlled by a control switch of the remote controller to show different test patterns for testing the user's visual acuity, the remote controller having a plurality of direction buttons through which the user gives an answer to every test pattern shown on the display module, the mainframe further having a visual acuity display unit controlled to indicate the user's visual acuity by digital and alphabet, and a buzzer controlled to give a particular sound after test of every test pattern subject to the test result.

8 Claims, 5 Drawing Sheets

REMOTE-CONTROLLED LCD SIGHT-TESTING INSTRUMENT

BACKGROUND OF THE INVENTION

The present invention relates to an instrument for testing eyesight, and more particularly to a remote-controlled LCD sight-testing instrument which is remote-controlled to show different test patterns for testing the user's visual acuity, and to indicate test result by digital.

In the ophthalmologic department of a hospital or an eye clinic, there is provided a sight-testing chart and illuminated by a light source for testing eyesight. This sight-testing chart has a plurality of test patterns of different sizes marked on it. The test patterns show a respective gap in different directions. The eye patient is requested to point out the direction of the gap at the assigned test pattern. This eyesight testing method has drawbacks as outlined hereinafter.

1. Because the test patterns are aligned longitudinally as well as transversely, the directions of the gaps at the test patterns can easily be memorized after several tests.

2. This eyesight testing method must be performed under the guide of the examiner, i.e., the eye patient cannot make a test accurately by oneself.

3. Because the sight-testing chart is hung on the wall, it tends to be covered with dust and dirt.

4. Because a big number of test patterns of different sizes are aligned transversely as well as longitudinally on the front side of the sight-testing chart, the size of the sight-testing chart cannot be minimized without affecting test accuracy.

SUMMARY OF THE INVENTION

The present invention has been accomplished to provide a remote-controlled LCD sight-testing instrument which eliminates the aforesaid drawbacks. It is one object of the present invention to provide a remote-controlled LCD sight-testing instrument which is remote-controlled by the eye patient to achieve the test. It is another object of the present invention to provide a remote-controlled LCD sight-testing instrument which enables the user to complete the test by oneself without the assistance of another person. It is still another object of the present invention to provide a remote-controlled LCD sight-testing instrument which has an attractive outer appearance, and is easy to clean. It is still another object of the present invention to provide a remote-controlled LCD sight-testing instrument which is compact and portable, and needs less installation space. To achieve these and other objects of the present invention, there is provided a remote-controlled LCD sight-testing instrument which comprises a mainframe and a remote controller. The mainframe comprises an infrared receiver, a micro controller, and a display module. The display module comprises a plurality of annular display areas concentrically arranged at a front display face thereof and respectively divided into a plurality of display units. The display units are respectively driven by the micro controller subject to the nature of the infrared signal received by the infrared receiver, to show "on" or "off" status, causing a test pattern to be shown on the front display face of the display module. The remote controller comprises an infrared emitter, a control switch, and a plurality of direction buttons. The control switch is operated by the user to control the micro controller through the infrared emitter and the infrared receiver, causing the micro controller to drive the display module in showing a test pattern for testing the user's visual acuity. The direction buttons are operated by the user to give an answering signal to the micro controller through the infrared emitter and the infrared receiver. Test result is shown by digital or alphabet through a counter and a visual acuity display.

DETAILED DESCRIPTION OF THE PREFERRED EMBODIMENT

Figure 1:
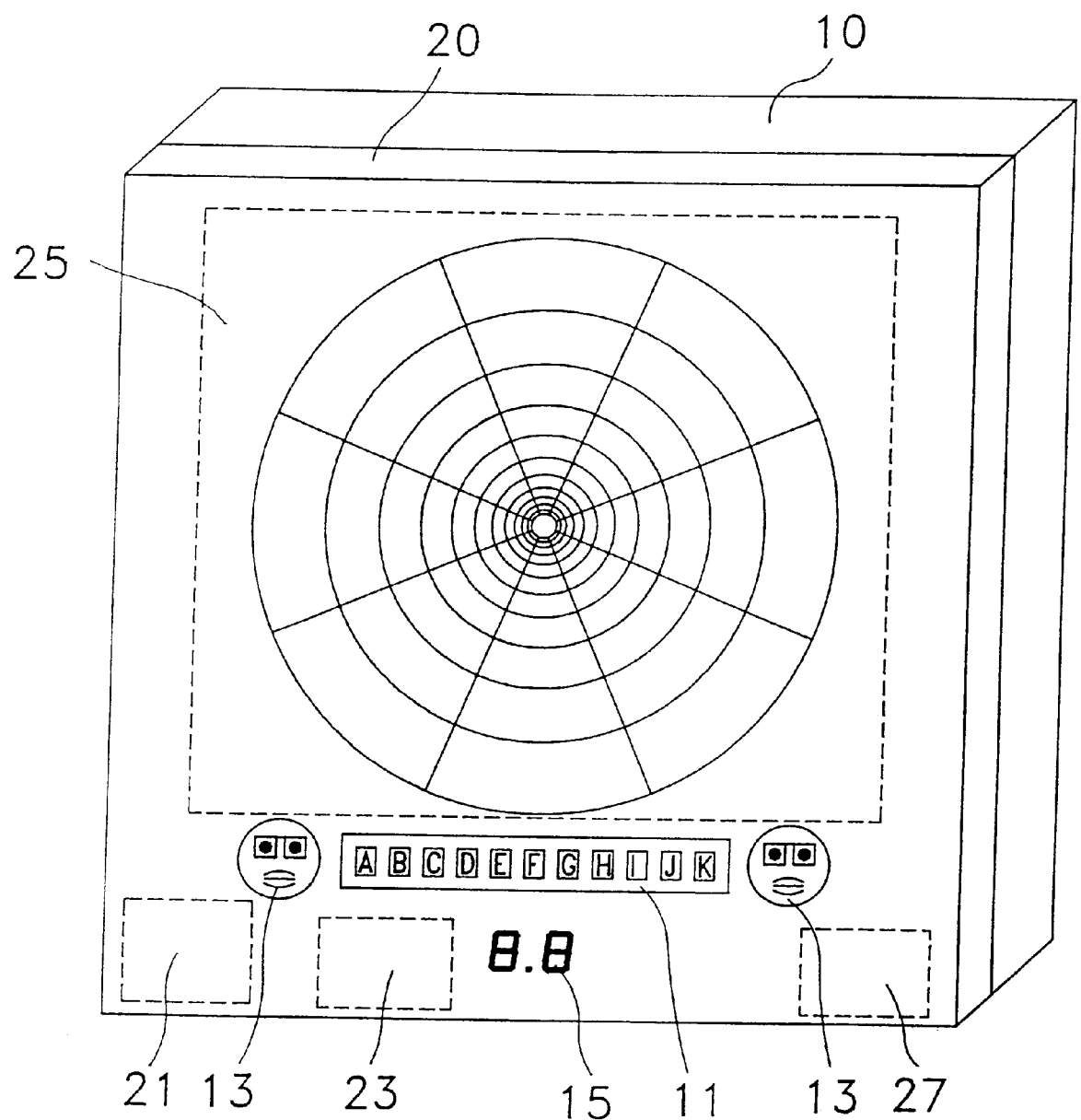
FIG. 1 is a perspective view of a remote-controlled LCD sight-testing instrument according to the present invention (the remote controller excluded).
Figure 2:
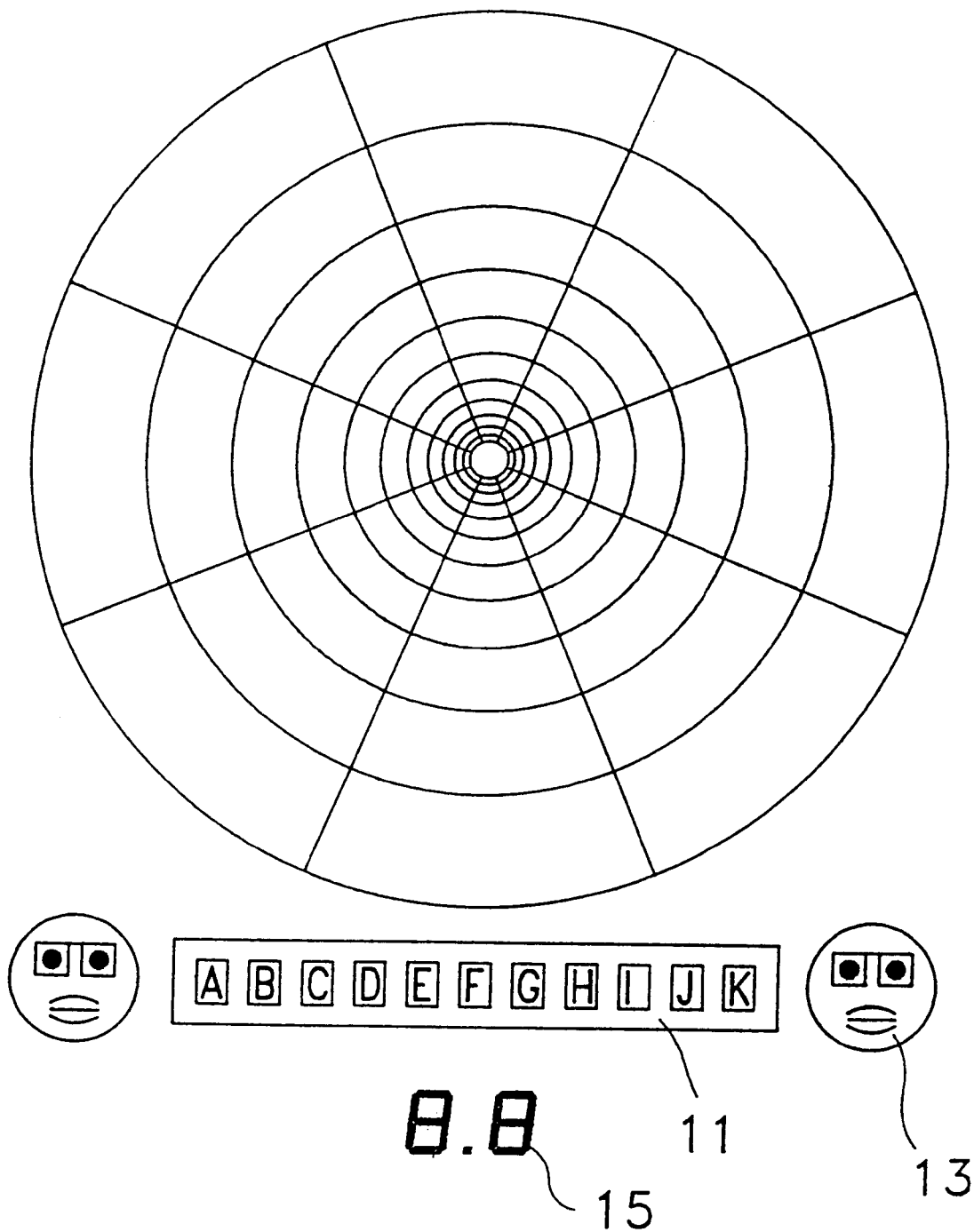
FIG. 2 is a front plain view of the LCD module for the remote-controlled LCD sight-testing instrument shown in FIG. 1.

Referring to FIGS. 1 and 2, a remote-controlled LCD sight-testing instrument in accordance with the present invention is generally comprised of a mainframe 10, and a flat LCD module 20. The mainframe 10 comprises an infrared receiver 21, a micro controller 23, a LCD driver 25, and a buzzer 27. The LCD module 20 comprises a visual acuity display unit 11 for indicating the degree of the eye patient's visual acuity by alphabet, a pattern display unit 13 for showing a test result pattern, and a counter 15 for indicating the eye patient's visual acuity by digital. The LCD module 20 has a plurality of annular liquid crystal display areas concentrically arranged at its front side, and respectively divided into a plurality of display units. Alternatively, the light emitting diodes can be arranged at the front side of the LCD module 20 instead of annular liquid crystal display areas. The display units of the LCD module 20 are respectively controlled by the micro controller 23 to show "on" or "off" status. Therefore, particular display units of the LCD module 20 can be turned to "on" status to show a test pattern "C" on the front side of the LCD module 20.

Figure 3:
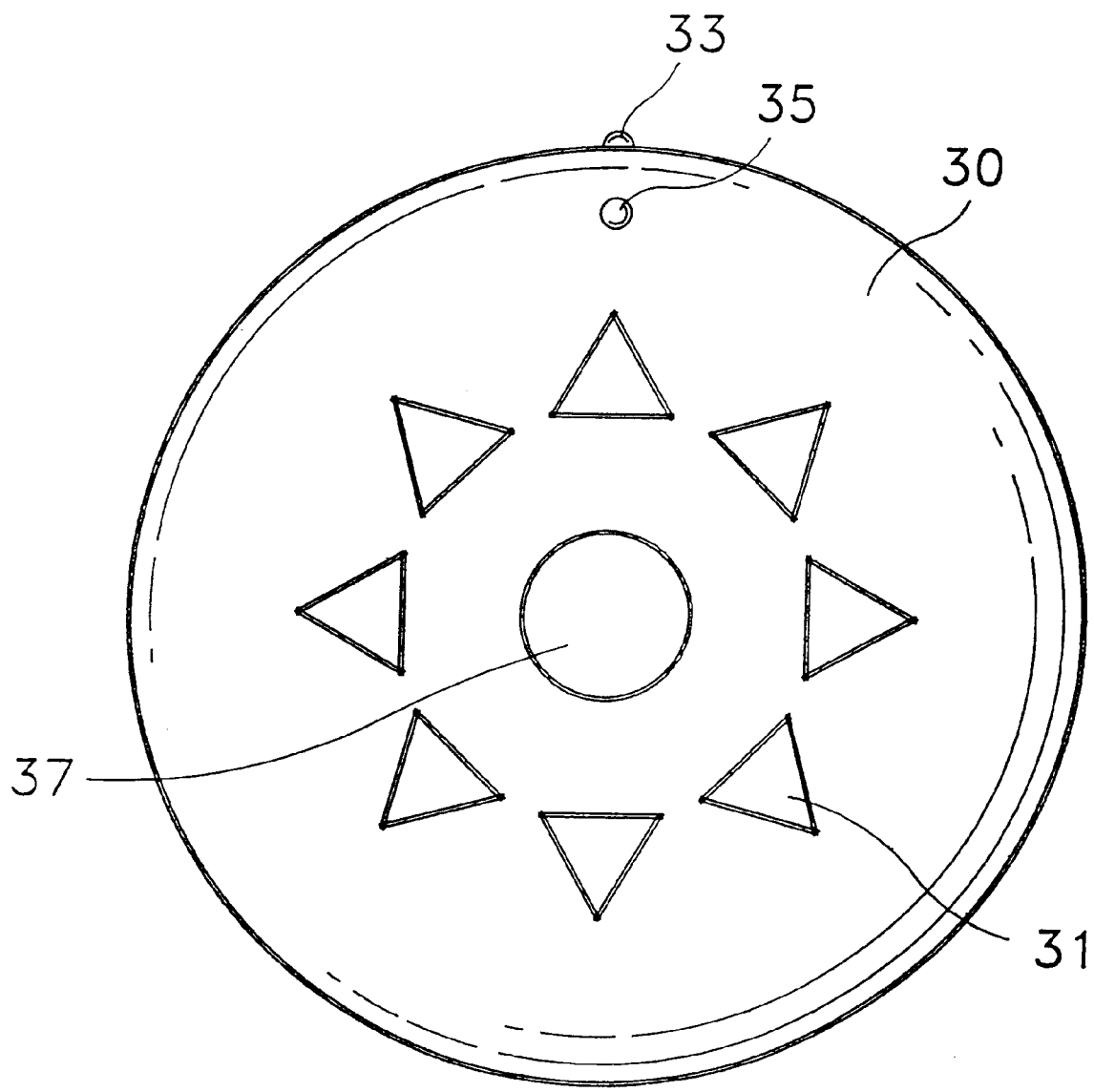
FIG. 3 is a plain view of the remote controller according to the present invention.

Referring to FIG. 3, a remote controller 30 comprises an infrared emitter 33, a plurality of direction buttons 31, a control switch 37, and an indicator light 35. The infrared emitter 33 is controlled by the control switch 37 and the direction buttons 31 to emit a respective infrared signal to the infrared receiver 21. When the infrared receiver 21 receives an infrared signal from the remote controller 30, it immediately transmits the signal to the micro controller 23 for processing. The direction buttons 31 are for the eye patient to give an answer to each test pattern shown on the LCD module 20.

Figure 4:
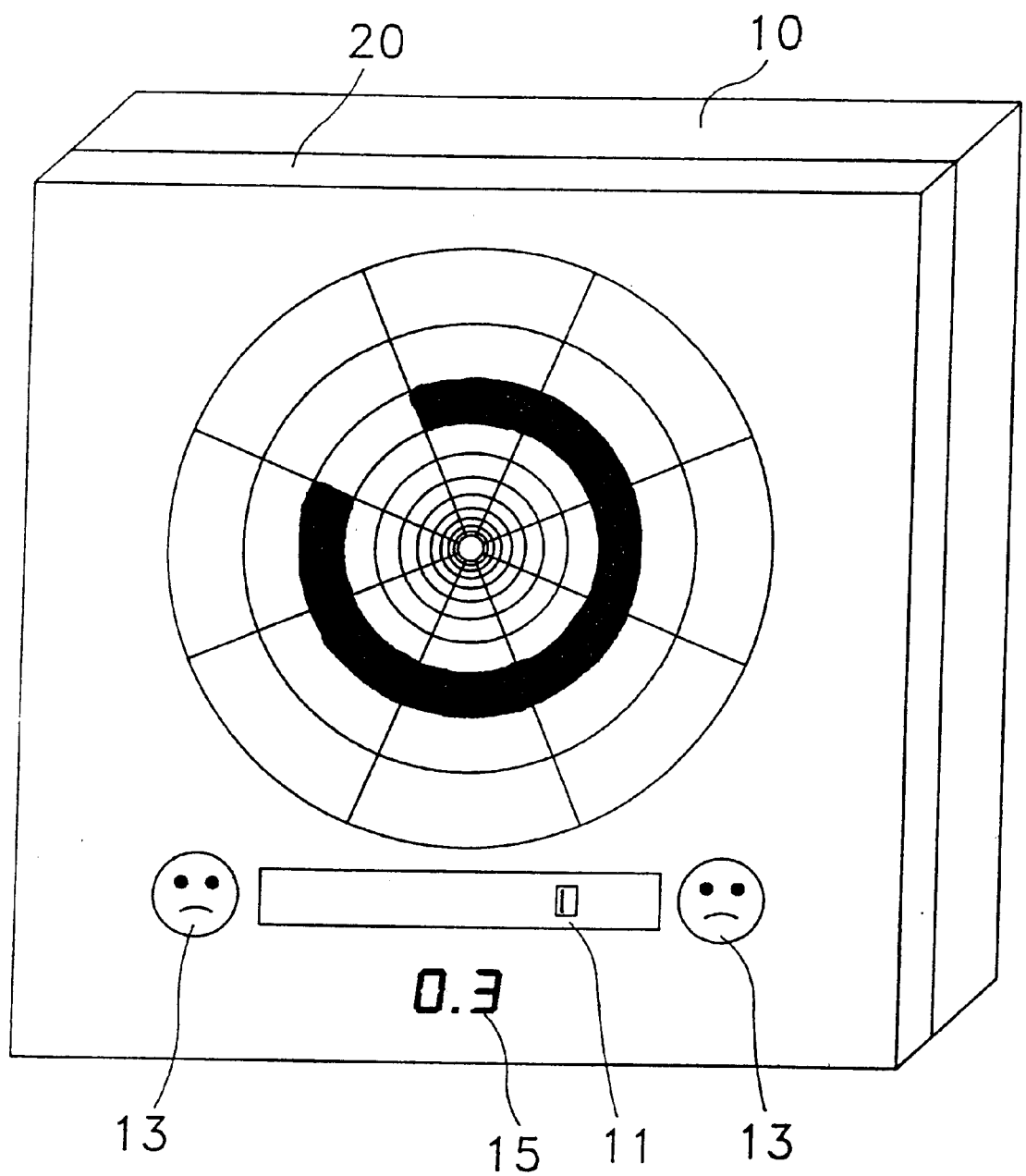
FIG. 4 shows a test example of the present invention.
Figure 5:
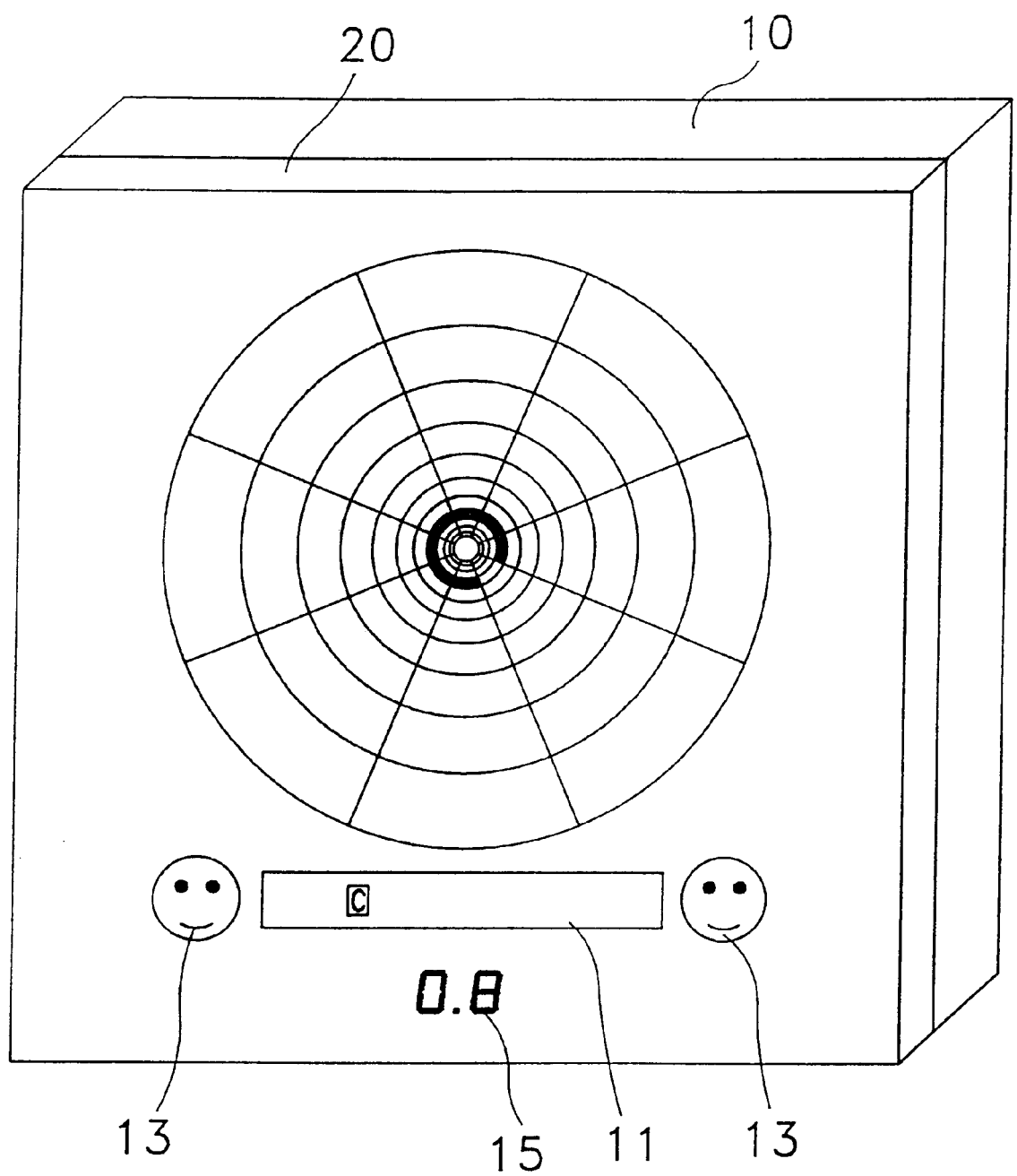
FIG. 5 shows another test example of the present invention.

Referring to FIGS. 4 and 5 and FIG. 3 again, when the control switch 37 is switched on, the mainframe 10 is at the stand-by status, and the LCD driver 25 is controlled by the micro controller 23 of the mainframe 10 to drive the LCD module 20, causing it to show randomly a set of test patterns one after another at a predetermined interval. When a test pattern is shown on the LCD module 20, the eye patient is requested to give an answer by controlling the corresponding direction button 31. If the correct direction button 31 is clicked, the micro controller 23 immediately drives the buzzer 27 to produce a particular sound, and then drives the LCD module 20 to change the test pattern. If a wrong direction button 31 is clicked, the micro controller 23 drives the buzzer 27 to produce another sound, and then drives the LCD module 20 to change the test pattern. If a plurality of wrong answers are continuously appeared, the micro controller 23 stops the test, and drives the visual acuity display unit 11 to indicate the degree of the eye patient's visual acuity by alphabet, the pattern display unit 13 to show a particular test result pattern for example a crying face, and the counter 15 to indicate the degree of the eye patient's visual acuity by digital.

While only one embodiment of the present invention has been shown and described, it will be understood that various modifications and changes could be made thereunto without departing from the spirit and scope of the invention disclosed.

What the invention claimed is:

1. A remote-controlled LCD sight-testing instrument comprising a mainframe and a remote controller, said mainframe comprising an infrared receiver, a micro controller, and a display module, said display module comprising a plurality of annular display areas concentrically arranged at a front display face thereof and respectively divided into a plurality of display units, said display units being respectively driven by said micro controller subject to the nature of the infrared signal received by said infrared receiver, to show "on" or "off" status, causing a test pattern to be shown on the front display face of said display module, said remote controller comprising an infrared emitter, a control switch, and a plurality of direction buttons, said control switch being operated by the user to control said micro controller through said infrared emitter and said infrared receiver, causing said micro controller to drive said display module in showing a test pattern for testing the user's visual acuity, said direction buttons being operated by the user to give an answering signal to said micro controller through said infrared emitter and said infrared receiver.

2. The remote-controlled LCD sight-testing instrument of claim 1, wherein the front display face of said display module is a liquid crystal display.

3. The remote-controlled LCD sight-testing instrument of claim 2, wherein said display module further comprises a visual acuity display unit controlled to indicate the test result by alphabet and digital.

4. The remote-controlled LCD sight-testing instrument of claim 2, wherein said display module further comprises a pattern display controlled to indicate the test result by a pattern.

5. The remote-controlled LCD sight-testing instrument of claim 1, wherein the front display face of said display module is a formed of a circuit board and a plurality of light emitting diodes on said circuit board.

6. The remote-controlled LCD sight-testing instrument of claim 1, wherein said mainframe further comprises a buzzer controlled by said micro controller to produce sound.

7. The remote-controlled LCD sight-testing instrument of claim 1, wherein said micro controller is programmed to produce a set of test patterns through the LCD module.

8. The remote-controlled LCD sight-testing instrument of claim 1, wherein said remote controller further comprises an indicator light which is turned on when said control switch or one of said direction button is operated.

* * * * *